United States Patent [19]

Lindel et al.

[11] Patent Number: 4,988,694
[45] Date of Patent: Jan. 29, 1991

[54] 4-BROMO-6-CHLORO-5-AMINO-2-PYRIDYL-ETHANOLAMINES AND THEIR USE AS YIELD PROMOTERS

[75] Inventors: Hans Lindel, Leverkusen; Werner Hallenbach, Langenfeld; Friedrich Berschauer, Wuppertal; Gernot Klotz, Leichligen; Heinrich A. Greife, Langenfeld, all of Fed. Rep. of Germany

[73] Assignee: Bayer Aktiengesellschaft, Leverkusen, Fed. Rep. of Germany

[21] Appl. No.: 340,936

[22] Filed: Apr. 20, 1989

[30] Foreign Application Priority Data

Apr. 23, 1988 [DE] Fed. Rep. of Germany ....... 3813839

[51] Int. Cl.$^5$ ................. C07D 213/74; C07D 405/06; C07D 401/06; A61K 31/44
[52] U.S. Cl. ................. 514/235.5; 514/252; 514/318; 514/343; 514/352; 544/124; 544/360; 546/14; 546/187; 546/281; 546/312
[58] Field of Search ............. 546/14, 312, 187, 28.1; 544/124, 360, 229; 514/235.5, 252, 318, 343, 352

[56] References Cited

U.S. PATENT DOCUMENTS

| | | | |
|---|---|---|---|
| 4,358,455 | 11/1982 | Atkinson et al. | 424/263 |
| 4,686,222 | 8/1987 | Atkinson et al. | 514/255 |
| 4,816,457 | 3/1989 | Atkinson et al. | 514/256 |

Primary Examiner—Mary C. Lee
Assistant Examiner—Jacqueline Haley
Attorney, Agent, or Firm—Sprung, Horn, Kramer & Woods

[57] ABSTRACT

4-Bromo-6-chloro-5-amino-2-pyridyl-ethanolamines, intermediates for preparation thereof and their use as yield promoters for animals and as feedstuff additives to achieve higher increases in weight and improved feed utilization of the formula

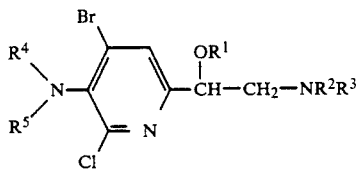

in which
$R^1$ stands for hydrogen, alkyl, acyl or substituted silyl,
$R^2$ stands for hydrogen or alkyl,
$R^3$ stands for hydrogen, alkyl, cycloalkyl, substituted alkyl, optionally substituted aralkyl, aryl or heterocyclyl, or
$R^2$ and $R^3$, together with the nitrogen atom to which they are bonded, can stand for an optionally substituted heterocyclic radical,
$R^4$ stands for hydrogen or alkyl and
$R^5$ stands for hydrogen, alkyl, halogenoalkyl or acyl, and their physiologically tolerated salts and their N-oxides have been found.

5 Claims, No Drawings

4-BROMO-6-CHLORO-5-AMINO-2-PYRIDYL-ETHANOLAMINES AND THEIR USE AS YIELD PROMOTERS

The present invention relates to 4-bromo-6-chloro-5-amino-2-pyridyl-ethanolamines, processes for their preparation, intermediate products for these and their use as yield promoters for animals.

The use of feedstuff additives to achieve higher increases in weight and improved feed utilization is already widely practised in animal nutrition, especially in the fattening of pigs, cattle and poultry.

1. New 4-bromo-6-chloro-5-amino-2-pyridyl-ethanolamines of the formula (I)

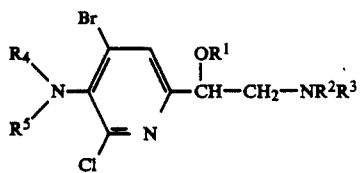

in which $R^1$ stands for hydrogen, alkyl, acyl or substituted silyl, $R^2$ stands for hydrogen or alkyl, $R^3$ stands for hydrogen, alkyl, cycloalkyl, substituted alkyl, optionally substituted aralkyl, aryl or heterocyclyl, or $R^2$ and $R^3$, together with the nitrogen atom to which they are bonded, can stand for an optionally substituted heterocyclic radical, $R^4$ stands for hydrogen or alkyl and $R^5$ stands for hydrogen, alkyl, halogenoalkyl or acyl, and their physiologically tolerated salts and their N-oxides have been found.

2. A process has been found for the preparation of the 4-bromo-6-chloro-5-amino-2-pyridyl-ethanolamines of the formula (I)

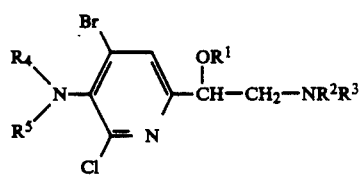

in which $R^1$ stands for hydrogen, alkyl, acyl or substituted silyl, $R^2$ stands for hydrogen or alkyl, $R^3$ stands for hydrogen, alkyl, cycloalkyl, substituted alkyl, optionally substituted aralkyl, aryl or heterocyclyl, or $R^2$ and $R^3$, together with the nitrogen atom to which they are bonded, can stand for an optionally substituted heterocyclic radical, $R^4$ stands for hydrogen or alkyl and $R^5$ stands for hydrogen, alkyl, halogenoalkyl or acyl, which is characterized in that beta-chloroethyl compounds of the formula (II)

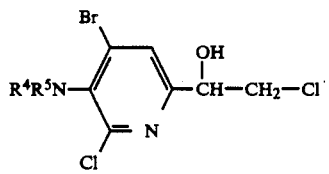

in which $R^4$ and $R^5$ have the abovementioned meaning, are reacted with amines of the formula (III)

$$HNR^2R^3 \qquad (III)$$

in which $R^2$ and $R^3$ have the abovementioned meaning, and if appropriate the products are then alkylated, acylated or silylated.

3. 4-Bromo-5-amino-6-chloro-2-pyridyl-monochloro-ethanol of the formula (II)

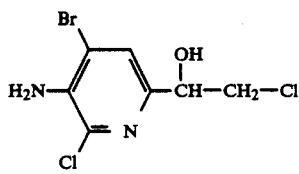

in new.

4. Process for the preparation of 4-bromo-5-amino-6-chloro-2-pyridylmonochloroethanol of the formula (II) according to 3 (above), characterized in that 4-bromo-5-amino-6-chloro-2-chloroacetyl-pyridine of the formula (IV)

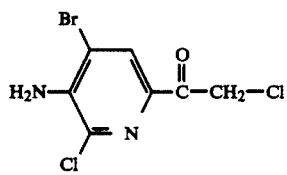

is reduced.

5. The compound of the formula (IV)

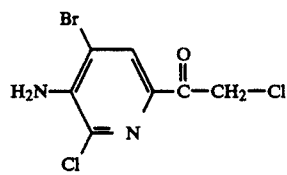

is new.

6. Process for the preparation of the compound of the formula (IV) according to 5 (above), characterized in that the compound of the formula (IV)

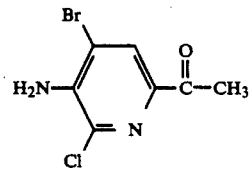

is chlorinated.

7. The compound of the formula (V)

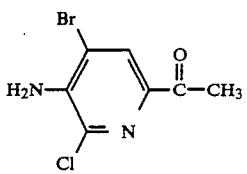
(V)

is new.

8. Process for the preparation of the compound of the formula (V) according to 7 (above), characterized in that the compound of the formula (VI)

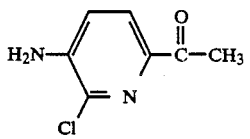
(VI)

is brominated.

9. The compound of the formula (VI)

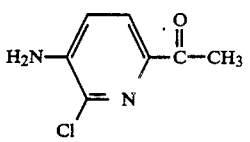
(VI)

is new.

10. Process for the preparation of the compound of the formula (VI) according to 9 (above), characterized in that the compound of the formula (VII)

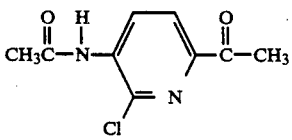
(VII)

is hydrolyzed.

11. The compound of the formula (VII)

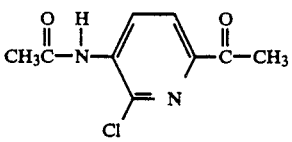
(VII)

is new.

12. Process for the preparation of the compound of the formula (VII) according to 11 (above), characterized in that the compound of the formula (VIII)

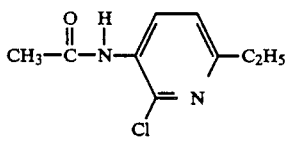
(VIII)

is oxidized.

13. The compound of the formula (VIII)

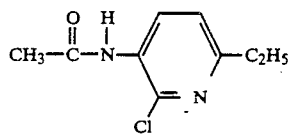
(VIII)

is new.

14. Process for the preparation of the compound of the formula (VIII) according to 13 (above), characterized in that the compound of the formula (IX)

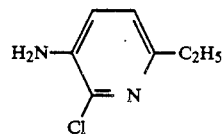
(IX)

is acetylated.

15. The compound of the formula (IX)

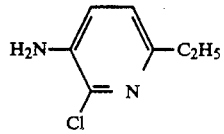
(IX)

is new.

16. Process for the preparation of the compound of the formula (IX) according to 15 (above), characterized in that the compound of the formula (X)

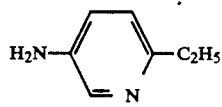
(X)

is chlorinated.

The compounds of the formula (I) are used as yield promoters for animals. In particular, they have the effect of shifting the meat/fat ratio in favor of meat and can therefore be used in animal rearing and animal nutrition.

The compounds of the formula (I) can exist in the form of their racemates or enantiomeric forms.

Physiologically tolerated salts of the compounds of the formula I can be formed with the following acids: hydrochloric acid, sulphuric acid, phosphoric acid, perchloric acid, hydrobromic and hydroiodic acid, nitric acid, acetic acid, oxalic acid, malonic acid, succinic acid, ascorbic acid, malic acid, tartargic acid, maleic acid, fumaric acid, methanesulphonic acid, benzoic acid, substituted benzoic acids, formic acid, toluenesulphonic acid, benzenesulphonic acid, phthalic acid, naphthalenesulphonic acid, nicotinic acid, palmitic acid and embonic acid.

Preferred compounds of the formula (I) are those in which $R^1$ stands for hydrogen or $C_{1-6}$-alkyl, or for carbonyl-$C_{1-6}$-alkyl, optionally substituted carbonylphenyl, sulphonyl-$C_{1-6}$-alkyl or optionally substituted sulphonylphenyl, or for tris-($C_1$–$C_{12}$-alkyl)-silyl or diphenyl-$C_{1-6}$-alkyl-silyl, $R^2$ stands for hydrogen or $C_{1-6}$-alkyl, $R^3$ stands for hydrogen, optionally substituted branched $C_{3-6}$-alkyl, $C_{3-6}$-cycloalkyl or $C_{1-6}$-alkylphenyl, or $R^2$ and $R^3$, together with the nitrogen atom to which they are bonded, can stand for an optionally substituted 5- to 6-membered saturated or unsaturated heterocyclic radical which can optionally also contain further hetero atoms from the series comprising N, O and S, $R^4$ stands for hydrogen or $C_{1-6}$-alkyl and $R^5$ stands for hydrogen, $C_{1-6}$-alkyl, $C_{1-4}$-halogenoalkyl, $C_{1-6}$-alkylcarbonyl, optionally substituted benzoyl, $C_{1-6}$-alkylsulphonyl or optionally substituted phenylsulphonyl.

Preferred possible substituents of the optionally substituted radicals are: cyano, halogen, such as fluorine or chlorine, hydroxyl, $C_{1-4}$-alkyl, $C_{1-4}$-halogenoalkyl, phenyl, $C_{1-4}$-alkoxy, $C_{1-4}$-halogenoalkoxy, $C_{1-4}$-alkylthio and $C_{1-4}$-halogenoalkylthio, and in the case where the substituents are on a phenyl radical, also preferably methylenedioxy, ethylenedioxy, halogen-substituted methylenedioxy and halogen-substituted ethylenedioxy, and furthermore phenyl and phenoxy, which can in turn carry one or more of the abovementioned substituents.

Particularly preferred compounds of the formula (I) are those in which $R^1$ stands for hydrogen or $C_{1-6}$-alkyl, in particular methyl or ethyl, $R^2$ stands for hydrogen or $C_{1-4}$-alkyl, in particular methyl or ethyl, $R^3$ stands for hydrogen, branched $C_{3-6}$-alkyl which is optionally substituted by 1 to 5 halogen atoms, in particular i-propyl, t-butyl, pentyl and hexyl, secondary and tertiary alkyl radicals being mentioned in particular, or $C_{1-6}$-alkylphenyl, which can optionally be substituted in the phenyl ring by halogen, in particular fluorine or chlorine, $C_{1-4}$-alkyl, hydroxyl, $C_{1-4}$-alkoxy or optionally halogen-substituted methylenedioxy or ethylenedioxy, $R^4$ stands for hydrogen and $R^5$ stands for hydrogen.

The following compounds of the formula (I) may be mentioned specifically:

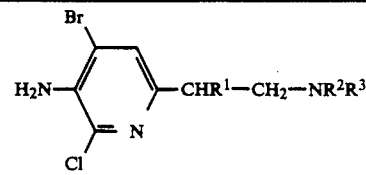

| $R^1$ | $R^2$ | $R^3$ |
|---|---|---|
| OH | H | i-$C_3H_7$ |
| $OCH_3$ | H | i-$C_3H_7$ |
| OH | H | t-$C_4H_9$ |
| OH | H | t-$C_4H_8F$ |
| OH | H | 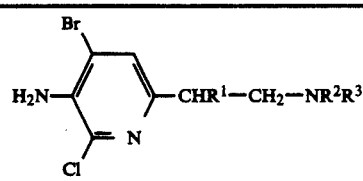 |
| OH | H | 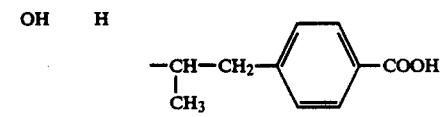 |
| OH | H | 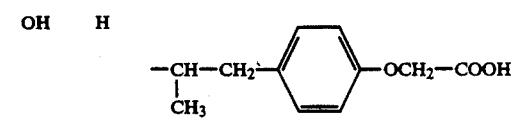 |

The salts with hydrochloric acid, sulphuric acid, phosphoric acid, oxalic acid, maleic acid, fumaric acid and malonic acid may be mentioned as preferred.

If 4-bromo-5-amino-6-chloro-2-(1-hydroxy-2-chloroethyl)-pyridine is used as the beta-halogenoethyl compound of the formula (II) and t-butylamine is used as the amine of the formula (III) for the preparation of the 4-bromo-6-chloro-5-amino-2-pyridyl-ethanolamines, the process for the preparation of the compound of the formula (I) can be represented by the following equation:

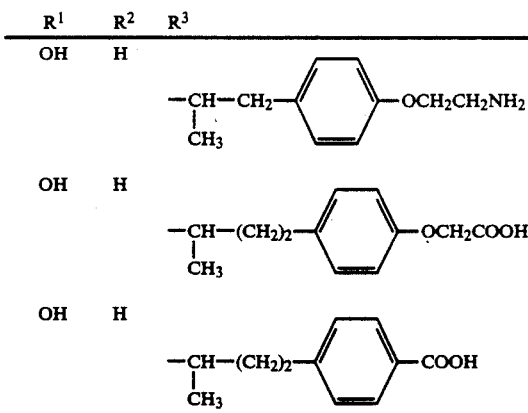

Beta-halogenoethyl compounds of the formula (II) are new. Their preparation is described below.

The following compounds of the formula (II) may be mentioned specifically:

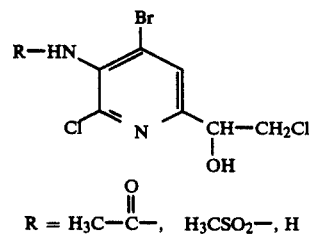

$R = H_3C-\overset{\overset{O}{\|}}{C}-, \quad H_3CSO_2-, \quad H$

Preferred amines of the formula (III) which may be mentioned are: ammonia, methylamine, dimethylamine, ethylamine, diethylamine, methylethylamine, n-propylamine, amine, i-propylamine, n-butylamine, i-butylamine, tert.-butylamine, cyclopentylamine, cyclohexylamine, benzylamine, aniline, piperidine, pyrrolidine, morpholine, 2-aminopyridine, 3-(4-carbomethoxyphenyl)-2-propylamine, 3-(4-methoxycarbonylmethoxyphenyl)-2-propylamine, 3-(4-carboxyphenyl)-2-propylamine, 3-(4-carboxymethoxyphenyl)-2-propylamine, 3-(4-hydroxymethylphenyl)-2-propylamine and 3-(4-(2-hydroxyethyl)-phenyl)-2-propylamine.

The process is carried out by reacting the betahalogenoethyl compound of the formula (II) with excess amine of the formula (III), if appropriate in the presence of a diluent.

The amine of the formula (III) is employed in a 2–10 molar, preferably 2–3 molar, excess.

The reaction is carried out at temperature from +20° to +250° C., preferably at between 50° and 150° C.

The reaction is carried out under normal pressure or, especially in the case of volatile amines, under increased pressure.

All the inert organic solvents serve as the diluent. These include, in particular, aliphatic and aromatic, optionally halogenated hydrocarbon, such as pentane, hexane, cyclohexane, benzene, toluene, methylene chloride and chloroform, and furthermore ethers, such as diethyl ether, tetrahydrofuran and dioxane, and moreover nitriles, such as acetonitrile and benzonitrile, and furthermore amides, such as dimethylformamide, and furthermore alcohols, such as methanol, ethanol and n- and i-propanol.

Alcohols are preferably employed.

Working up is carried out by distilling off excess amine and the solvent. The compounds are purified by crystallization.

Process 4 for the preparation of the compounds of the formula (II) can be represented by the following equation:

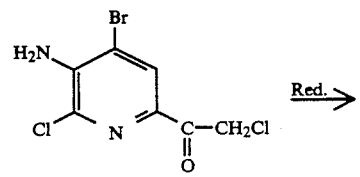

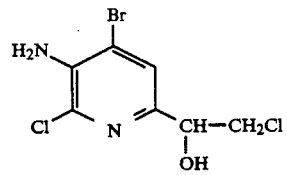

The process is carried out by reacting the compound of the formula (IV) with the reducing agent in a diluent.

Complex hydrides, such as sodium borohydride and lithium borohydride and, in addition, diborane, serve as the reducing agent.

The reaction is carried out at temperatures from −20° C. to +100° C.

The reaction is preferably carried out under normal pressure.

All the inert organic solvents serve as the diluent. These include, in particular, optionally halogenated aliphatic and aromatic hydrocarbons, such as pentane, hexane, cyclohexane, benzene, toluene, methylene chloride, chloroform and chlorobenzene; ethers, such as diethyl ether and tetrahydrofuran; nitriles, such as acetonitrile and benzonitrile; and alcohols, such as methanol, ethanol and n- and i-propanol. Alcohols are preferably used.

Process 6 for the preparation of the compound of the formula (IV) can be represented by the following equation:

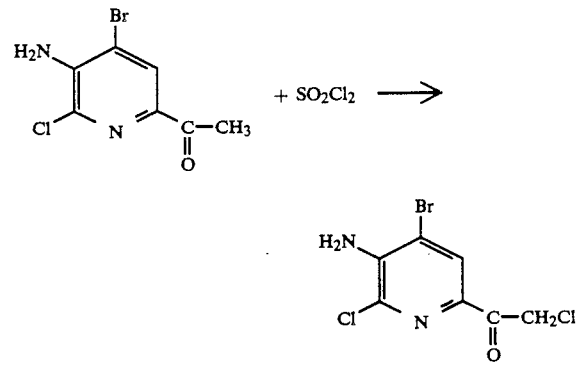

The process is carried out by adding 1–3 mol, preferably 1–1.5 mol, of halogenating agent, if appropriate in the presence of a diluent, per mol of compound of the formula (V).

Sulphuryl chloride, chlorine and N-chloro compounds, such as, for example, N-chlorosuccinimide, serve as the halogenating agent. Sulphuryl chloride is preferred.

The reaction is carried out at between −20° C. and +150° C., preferably between 0° C. and 70° C.

The reaction is preferably carried out under normal pressure.

Diluents which may be mentioned are: aliphatic, optionally halogenated hydrocarbons, such as pentane, hexane, heptane, cyclohexane, methylene chloride, ethylene chloride, chloroform and carbon tetrachloride, alcohols, such as methanol and ethanol, esters, such as ethyl acetate, and mixtures of these diluents.

Process 8 for the preparation of the compound of the formula (V) can be represented by the following equation:

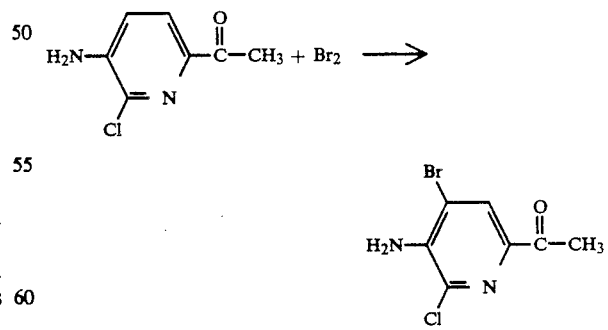

The process is carried out by reacting the compound of the formula (VI) with bromine or a brominating agent in the presence of a diluent.

The reaction is carried out at temperatures between −20° C. and +150° C., preferably between 0° C. and 70° C.

Approximately the equivalent amount of bromine or brominating agent is employed per mol of the compound of the formula (VI).

Diluents which may be mentioned are aliphatic, optionally halogenated hydrocarbons, such as, for example pentane, hexane, heptane, cyclohexane, methylene chloride, ethylene chloride, chloroform and carbon tetra-chloride, alcohols, such as methanol and ethanol, esters, such as ethyl acetate, and glacial acetic acid.

Working up is carried out in the customary manner, for example by distilling off the diluent.

Process 10 for the preparation of the compound of the formula (VI) can be represented by the following equation:

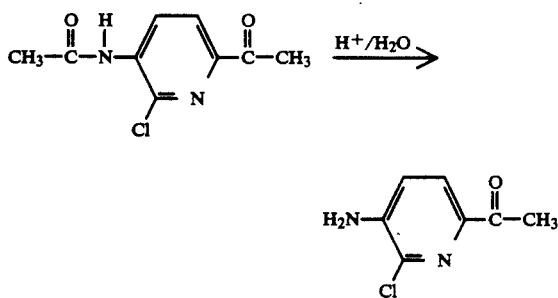

The process is carried out by treating the compound of the formula (VII) with acids, if appropriate in the presence of a diluent.

HCl, $H_2SO_4$, HBr, $H_3PO_4$, methanesulphonic acid, benzenesulphonic acid or strongly acid ion exchangers serve as the acids.

Water and water-miscible solvents, such as, for example, alcohols, such as methanol, ethanol and i-propanol, and ketones, such as acetone, serve as the diluent. Alcohols are preferred.

The reaction is carried out at temperatures between 0° and 150° C., preferably between 50° and 120° C.

The reaction is preferably carried out under normal pressure.

Working up is carried out, after neutralization, by filtering off or extracting the compound of the formula (VI).

Process 12 for the preparation of the compound of the formula (VII) can be represented by the following equation:

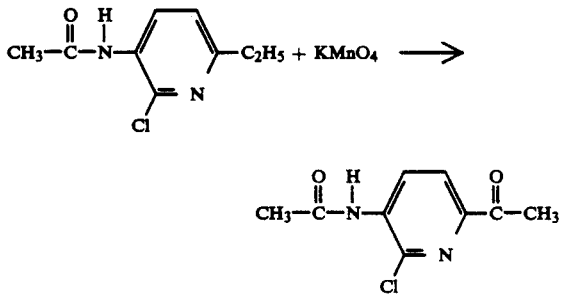

The process is carried out by oxidizing the compound of the formula (VIII) with potassium permanganate in water-containing diluents in the presence of buffer substances.

Water mixed with alcohols, such as for example, t-butanol, ketones, such as, for example, acetone, amines, such as, for example, pyridine, nitriles, such as, for example, acetonitrile, or ethers, such as, for example, diglycol dimethyl ether, serves as the diluent.

The reaction is carried out at pH values between 4 and 10, preferably between pH 5 and 8. These pH values are either established by continuously metering in an acid, such as, for example, acetic acid, or they are maintained in the presence of buffer substances, such as, for example, $NaH_2PO_4$, $Mg(NO_3)_2$ or $MgO/HNO_3$, $MgSO_4$, $CaSO_4$ or $NaHCO_3$.

1.1–6 mol of $KMnO_4$ and 1.1–6 mol of buffer substance, preferably in each case 1.1–3 mol, are employed per mol of the compound of the formula (VIII).

The reaction is carried out at temperature between 0° and 70° C., preferably between 10° and 30° C.

The reaction is carried out under normal pressure.

Working up is carried out by filtering off the manganese dioxide and distilling off the solvent from the filtrate.

Process 14 for the preparation of the compound of the formula (VIII) can be represented by the following equation:

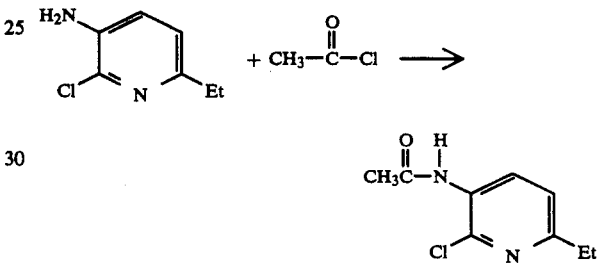

The following serve as the acylating agent: acetic anhydride, acetyl chloride and ketene.

The process according to the invention can be carried out with or without a diluent. Possible diluents are virtually all the inert organic solvents. These include, in particular, aliphatic and aromatic, optionally halogenated hydrocarbon, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl and dibutyl ether, glycol dimethyl ether and diglycol dimethyl ether, tetrahydrofuran and dioxane, and moreover ketones, such as acetone, methyl ethyl ketone, methyl isopropyl ketone and methyl isobutyl ketone, and in addition esters, such as methyl and ethyl acetate, and furthermore nitriles, such as, for example, acetonitrile, propionitrile, benzonitrile and glutaronitrile, and moreover amides, such as, for example, dimethylformamide, dimethylacetamide and N-methylpyrrolidone, as well as tetramethylene sulphone and hexamethylphosphoric acid triamide.

Catalysts and auxiliary bases can be added to accelerate the process according to the invention. Suitable catalysts and auxiliary bases are: for example Na acetate and tertiary amines, such as pyridine, 4-dimethylaminopyridine, triethylamine, triethylenediamine and trimethylene-tetrahydropyrimidine; and furthermore tin(II) and tin(IV) compounds, such as tin(II) octoate or tin(IV) chloride. The tertiary amines mentioned as reaction accelerations, for example pyridine, can also be used as solvents.

The reaction is carried out at temperatures from 0° to 250° C., preferably from 50° to 150° C.

The reaction is preferably carried out under normal pressure.

1–5 mol, preferably 1–2 mol, of acylating agent are employed per mol of the compound of the formula (IX). 1–5 mol, preferably 1–2 mol, of auxiliary base are employed per mol of the compound (IX). If used 0.01–1 mol of catalysts are employed per mol of the compound of the formula (IX).

The reaction mixture is diluted with water, extracted or filtered, and if appropriate the solvent is distilled off.

Process 16 for the preparation of the compound of the formula (X) can be represented by the following equation:

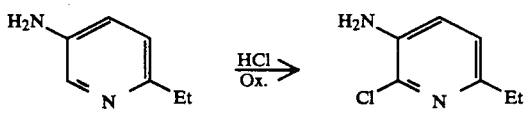

The reaction is carried out with hydrochloric acid in the presence of an oxidizing agent.

$H_2O_2$, salts and derivatives thereof, such as, for example, sodium peroxide, and peracids, such as aliphatic and aromatic peracids, preferably serve as the oxidizing agent. Such oxidizing agents which may be mentioned are: perpropionic acid and perbenzoic acid, which can optionally be substituted. Other oxidizing agents are salts or esters of hypochlorous acid, such as, for example, sodium hypochlorite, and potassium permanganate, manganese dioxide and peroxomono- and peroxodisulphates.

1–4 equivalents, particularly preferably 1–1.5 equivalents, of oxidizing agent are employed per mol of the compound (X).

The reaction is preferably carried out in aqueous solution. It can also be carried out in organic solvents which are inert towards the reaction conditions.

The process is carried out at temperature between 0° and 150° C., preferably between 10° and 100° C. and particularly preferably between 20° and 80° C.

The reaction is carried out under normal pressure.

However, the chlorination can also be carried out with sulphuryl chloride.

5-Amino-3-ethylpyridine is known. It can be prepared by a process analogous to that described by G. H. Cooper et al., J. Chem. Soc. C (1971), 3257–60, by reducing the corresponding nitro compound. The reduction here is carried out in aqueous solvent mixtures with hydrogen and palladium-on-active charcoal catalyst.

The active compounds are suitable as agents for yield promotion in animals for rearing and stock animals. They are used in this context for promoting and accelerating growth and milk and wool production and for improving the feed utilization and the quality of the meat and for shifting the meat/fat ratio in favor of meat.

Stock animals and animals for rearing include mammals, such as, for example, cattle, horses, sheep, pigs, goats, camels, water buffaloes, donkeys, rabbits, fallow deer and reindeer, fur-bearing animals, such as, for example, mink, chinchillas and racoons, birds, such as, for example, chickens, geese, turkeys and ducks, and fresh- and salt-water fish, such as, for example, trout, carp and eels.

The active compounds are used during all the growth and yield phases of the animals regardless of the sex of the animals. The active compounds are preferably used during the intensive growth and yield phase. The intensive growth and yield phase lasts from one month to 10 years, depending on the species of animal. The active compounds have proved particularly useful in the rearing and keeping of young and fattening animals.

The active compounds are used enterally or parenterally, directly or in the form of formulations suitable for animals. Enternal use of the active compounds is effected, for example, orally in the form of powders, tablets, capsules, pastes, drinks, granules or boli, via solutions, emulsions or suspensions for oral administration and via the food or via the drinking water. Parenteral use is effected, for example, in the form of an injection (intramuscular, subcutaneous or intravenous or by implants).

Formulations for administration via the feed or drinking water may be mentioned in particular. In this case, the active compounds can be added to the feed directly or in the form of premixes or feed concentrates.

Feed includes individual feedstuffs of vegetable origin, such as hay, beet, cereals and cereal by-products, molasses and silage, individual feedstuffs of animal origin, such as meat, fats, milk products, bonemeal and fish products, and individual feedstuffs such as vitamins, proteins, sugars, starches, flours, amino acids, for example DL-methionine, and salts, such as lime and sodium chloride. Feed also includes supplementary, ready-mixed and mixed feedstuffs. These contain individual feedstufs in a composition which ensures balanced nutrition in respect of energy and protein supply and and supply with vitamins, mineral salts and trace elements.

Premixes and feed concentrates are mixtures of the active compound with carriers and if appropriate other auxiliaries. The carriers include all the individual feedstuffs or mixtures thereof.

The active compounds can be present in the formulations by themselves or as a mixture with other yield-promoting active compounds, mineral feedstuffs, trace element compounds, vitamins, nitrogen-containing non-protein compounds, dyestuffs, antioxidants, aroma substances, emulsifiers, flow control auxiliaries, preservatives and pressing auxiliaries.

Other yield-promoting active compounds are, for example, antibiotics, such as tylosin and virginiamycin. Mineral feedstuffs are, for example, dicalcium phosphate, magnesium oxide and sodium chloride. Trace element compounds are, for example, iron fumarate, sodium iodide, cobalt chloride, copper sulphate, zinc oxide and selenium compounds. Vitamins are, for example, vitamin A, vitamin $D_3$ and vitamin E. Nitrogen-containing non-protein compounds are, for example, biuret and urea. Dyestuffs are, for example, carotinoids, such as canthaxanthine, zeaxanthine, capsanthine or dyestuffs which are approved for coloring foodstuffs. Antioxidants are, for example, ethoxyquin, butylhydroxy-toluene and ascorbic acid. Aroma substances are, for example, vanilla. Emulsifiers are, for example, esters of lactic acid and lecithin. Flow control auxiliaries are, for example, sodium stearate, calcium stearate, silicic acids, bentonite and ligninsulphonates.

Preservatives are, for example, propionic acid, calcium propionate, sorbic acid and ascorbic acid. Pressing auxiliaries are, for example, lignin-sulphonates and cellulose ethers.

The concentration of the active compounds in the feed is usually about 0.001–500 ppm, preferably 0.1–50 ppm.

The concentration of the active compounds in the premixes of feed concentrates is about 0.5 to 50 per cent by weight, preferably 1 to 20 per cent by weight.

The amount of active compounds administered to the animals to achieve the desired effect can be varied widely because of the favorable properties of the active compounds. It is preferably about 0.001 to 50 mg/kg, in particular 0.01 to 5 mg/kg of body weight per day. The appropriate amount of the active compound and the appropriate duration of the administration depend, in particular, on the species, age, sex, state of health and nature of housing and feeding of the animals, and can easily be determined by any expert.

The active compounds are administered to the animals by customary methods. The nature of the administration depends, in particular, on the nature, behavior and state of health of the animals.

The active compounds can be administered a single time. However, the active compounds can also be administered temporarily or continuously during the entire or during part of the growth and yield phase. In the case of continuous administration, they can be used once or more than once daily at regular or irregular intervals.

Example of the composition of a chick-rearing feed containing active compound according to the invention:

200 g of wheat, 340 g of maize, 361 g of shredded soya, 60 of beef tallow, 15 g of dicalcium phosphate, 10 g of calcium carbonate, 4 g of iodinated sodium chloride, 7.5 g of a vitamin/mineral mixture of the composition shown below and 2.5 g of active compound premix of the composition shown below give, after thorough mixing, 1 kg of feed.

1 kg of vitamin/mineral mixture contains: 600 I.U. of vitamin A, 100 I.U. of vitamin $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7\ H_2O$, 100 mg of $FeSO_4 \times 7\ H_2O$ and 20 mg of $CuSO_4 \times 5\ H_2O$, in cereal flour as the carrier.

1 kg of active compound premix contains 100 g of active compound and 900 g of wheat flour.

Example of the composition of a pig-rearing feed containing active compound according to the invention:

630 g of shredded cereal fodder (composed of 200 g of maize, 150 g of shredded barley, 150 g of shredded oats and 130 g of shredded wheat), 80 g of fish meal, 60 g of shredded soya, 60 g of tapioca flour, 38 g of brewer's yeast, 50 g of a vitamin/mineral mixture (composition as for the chick feed) 30 g of linseed cake flour, 30 g of maize gluten feed, 10 g of soya oil, 10 g of cane sugar molasses and 2 g of active compound premix give, after thorough mixing, 1 kg of feed. 1 kg of active compound premix contains 200 g of active compound, 20 g of vegetable oil and 780 g of calcium carbonate powder.

Example of the composition of a feed for cattle containing the active compound according to the invention:

69.95% of shredded cereal fodder, 10% of ground maize stalks, 8% of soya bean flour, 5% of lucerne flour, 5% of molasses, 0.6% of urea, 0.5% of calcium phosphate, 0.5% of calcium carbonate, 0.3% of sodium chloride, 0.15% of vitamin/mineral mixture and 0.2% of active compound premix of the composition given for the pig-rearing food. The vitamin/mineral mixture contains, per kg, 70,000 I.U. of vitamin A, 70,000 I.U. of vitamin $D_3$, 100 mg of vitamin E, 50 mg of $MnSO_4 \times H_2O$ and 30 mg of $ZnSO_4 \times 7H_2O$ in cereal flour as the carrier.

The active compound premix is admixed to the vitamin/mineral mixture in the required amount and this mixture is then mixed thoroughly with the other constituents.

EXAMPLE

Rat-feeding experiment

Female laboratory rats weighing 90–110 g of the SPF wistar type (Hagemann breed) are fed ad libitum with standard rat food to which the desired amount of active compound has been added. Each experimental set-up is performed with food of an identical batch, so that differences in the composition of the food cannot impair the comparability of the results.

The rats are given water ad libitum.

An experimental group is formed from in each case 12 rats which are fed with food to which the desired amount of active compound has been added. A control group is given food without active compound. The experimental groups are composed so that the average body weight and the scatter in the body weights of the rats is the same in each experimental group, so that comparability of the experimental groups with one another is guaranteed.

Before the start of the experiment, the animals are adapted to the new housing conditions for 2 days, and during this period food is given without added active compound. Thereafter, the animals are given food containing active compound for 13 days. The relative increases in weight in relation to the untreated control is determined.

The results which can be seen from the table are obtained:

TABLE

Rat feeding experiment

| Active compound Example No | Active compound concentration ppm | Relative weight increase |
|---|---|---|
| 5 | 25 | 123 |
| 6 | 25 | 119 |
| 10 | 25 | 120 |
| 3 | 25 | 113 |
| 4 | 25 | 128 |
| 1 | 25 | 155 |

PREPARATION EXAMPLES

EXAMPLE 1

2-N-tert.-Butylamino-1-(3-amino-4-bromo-2-chloro-6-pyridyl)-ethanol 2 g (7 mmol) of 2-chloro-1-(3-amino-4-bromo-2-chloro-6-pyridyl)-ethanol and 1.28 g (17.5 mmol) of tert.-butylamine are dissolved in 10 ml of $CHCl_3$ and the solution is heated to 100° C. in an autoclave for 12 hours. For working up, the solution is partitioned between dilute NaOH and $CH_2Cl_2$ and the organic phase is separated off, dried and evaporated. The residue is partitioned between 5% strength $NaH_2PO_4$ and ether and the aqueous phase is separated off, rendered alkaline with NaOH and extracted three times with $CH_2Cl_2$. After drying with $Na_2SO_4$, the mixture is evaporated in vacuo. The residue is dissolved in ether, and petroleum ether is added until clouding starts. When the crystallization has ended, the product is filtered off with suction and washed with petroleum ether.
Yield: 660 mg (29% of theory)

Melting point: 122° C.
The following compounds are prepared analogously:

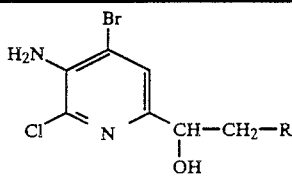

| Example No. | R | Melting point: (°C.) |
|---|---|---|
| 2 | —NH—C₆H₁₁ (cyclohexyl) | 88 |
| 3 | —NH—CH(CH₃)—CH₂—C₆H₄—O—CH₂—CH₂—OH | Oil IR: 3350, 2950, 1610, 1500, 1450, 1360, 1240, 1100, 1070, 1040, 720 cm⁻¹ |
| 4 | —NH—CH(CH₃)₂ | Oil IR: 3300, 2950, 1660, 1610, 1450, 1360, 1100, 1040, 870, 750 cm⁻¹ |
| 5 | —NH—CH(CH₃)—CH₂—O—CH₃ | 138 |
| 6 | —NH—CH(CH₃)—CH₂—C₆H₅ | Oil IR: 3350, 2950, 1600, 1560, 1530, 1450, 1360, 1030, 720 cm⁻¹ |
| 7 | —NH—(CH₂)₃CH₃ | 112 |
| 8 | —NH—CH(Et)₂ | Oil IR: 3350, 2950, 1600, 1560, 1530, 1450, 1360, 1100, 860, 750 cm⁻¹ |
| 9 | —NH—CH₂—CH(CH₃)₂ | 93 |
| 10 | —NH—C(CH₃)₂Et | 89 |
| 11 | —N(morpholino) | 118 |
| 12 | —NH—CH₂—CH₂—C₆H₄—OCF₃ | 65 |
| 13 | —N(N'-methylpiperazino) | 124 |

Example of process 4 for the preparation of the compound of the formula (II).

2-Chloro-1-(3-amino-4-bromo-2-chloro-6-pyridyl)-ethanol 1 g (4.52 mmol) of 3-amino-4-bromo-2-chloro-6-chloroacetylpyridine are suspended in 15 ml of methanol, the suspension is cooled to 0° C. and 133 mg (3.52 mmol) of $NaBH_4$ are added. After 10 minutes, the mixture is poured onto water, excess $NaBH_4$ is destroyed by acidification with HCl and the mixture is neutralized again with $NaHCO_3$. After extraction with $CH_2Cl_2$ and evaporation of the solvent, 1 g (99% of theory) is obtained as the residue.

Melting point: 30° C.

Example of process 6 for the preparation of the compound of the formula (IV).

3-Amino-4-bromo-2-chloro-6-chloroacetyl-pyridine 0.8 g (3.2 mmol) of 6-acetyl-3-amino-4-bromo-2-chloro-pyridine are dissolved in 5 ml of $CHCl_3$, and 462 mg (3.42 mmol) of $SO_2Cl_2$, dissolved in 5 ml of $CHCl_3$, are added. The mixture is stirred at room temperature for 30 minutes and then poured onto $NaHCO_3$ solution and extracted with $CH_2Cl_2$.

After the solvent has been evaporated off in vacuo, a brown solid remains.

Yield: 800 mg (88% of theory)
Melting point: 150° C.

Example for process 8 for the preparation of the compound of the formula (V).

6-Acetyl-3-amino-4-bromo-2-chloropyridine 15 g (88 mmol) of 6-acetyl-3-amino-2-chloropyridine are suspended in 88 ml of glacial acetic acid and 4.5 ml (88 mmol) of bromine are added dropwise. The mixture is subsequently stirred at room temperature for a further 30 minutes and then filtered off with suction and the filter cake is partitioned between $NaHCO_3$ solution and $CHCl_3$. The organic phase is separated off, dried with $Na_2SO_4$ and evaporated.

Yield: 13 g (60% of theory)
Melting point: 184° C.

Example for process 10 for the preparation of the compound of the formula (VI).

6-Acetyl-3-amino-2-chloropyridine 5 g (24 mmol) of 3-acetamido-6-acetyl-2-chloropyridine are boiled under reflux in a mixture of 25 ml of concentrated aqueous HCl and 25 ml of methanol for one hour. After cooling, the mixture is carefully added to 600 ml of saturated $NaHCO_3$ solution and extracted three times with 200 ml of methylene chloride each time. The collected organic phases are dried with $Na_2SO_4$ and evaporated. The residue is recrystallized from toluene/petroleum ether.

Yield: 3.4 g (84.5% of theory)
Melting point: 137° C. yellow crystals.

Example for process 12 for the preparation of the compound of the formula (VII).

6-Acetyl-3-acetamido-2-chloropyridine 4.937 g (0.124 mol) of MgO are suspended in 112 ml of water and the suspension is brought to pH 6 with about 16.7 ml (0.242 mol) of 65% strength $HNO_3$. 10 g (49.4 mmol) of 3-acetamido-2-chloro-6-ethylpyridine, dissolved in 112 ml of acetone, are then added, 19.5 g (0.124 mol of $KMnO_4$ are introduced and the mixture is stirred at 20° C. until the reaction is complete (48 hours). The solid is then filtered off with suction and the filter cake is washed thoroughly with hot acetone. The filtrate is diluted with 500 ml of water and extracted three times with 200 ml of $CHCl_3$ each time, and the combined extracts are washed with water, dried with $Na_2SO_4$ and evaporated. For purification, the product is recrystallized from toluene/petroleum ether.

Yield: 8.5 g (81% of theory)
Melting point: 183° C. colorless crystals.

Example for process 14 for the preparation of the compound of the formula (VIII).

3-Acetamido-2-chloro-6-ethylpyridine 27 g (173 mmol) of 3-amino-2-chloro-6-ethylpyridine are dissolved in 220 ml of dry $CHCl_3$ and 24.7 ml (177 mmol) of $Et_3N$ and 17.7 ml (187 mmol) of acetic anhydride are added. The mixture is left to stand at room temperature for 12 hours and is then heated under reflux for a further two hours.

For working up, the mixture is poured onto 400 ml of water and the organic phase is separated off and washed twice with 300 ml of $NaHCO_3$ solution each time. After drying with $Na_2SO_4$, the mixture is evaporated.

Yield: 28 g (82% of theory)
Melting point: 104° C.

Example for process 16 for the preparation of the compound of the formula (IX).

3-Amino-2-chloro-6-ethylpyridine 2 g (16.4 mmol) of 5-amino-2-ethylpyridine (for the preparation see G. H. Cooper and R. L. Rickard, J. Chem. Soc. C, 3257–60 (1971) are dissolved in 17.7 ml of concentrated HCl, and 2.2 ml (21.4 mol) of 30% strength $H_2O_2$ solution are then carefully added. An exothermic reaction starts. The temperature is kept at about 50° C. by cooling with an ice-bath, and when the reaction has subsided the mixture is subsequently stirred at this temperature for a further 15 minutes. For working up, the mixture is poured onto 200 ml of water, the pH is brought to 10 with 40% strength sodium hydroxidde solution and the mixture is extracted twice with 100 ml of methylene chloride each time. After drying with $Na_2SO_4$, the mixture is evaporated and the residue is stirred with petroleum ether and filtered off with suction.

Yield: 1.6 g (62.3% of theory)
Melting point: 104° C.

Example for the preparation of 5-amino-2-ethylpyridine:

40 g (0.263 mol) of 2-ethyl-5-nitropyridine are dissolved in a mixture of 400 ml of dioxane and 50 ml of water, 2 g of 10% strength Pd/active charcoal are added and the mixture is hydrogenated at room temperature and under normal pressure until the uptake of $H_2$ is complete.

The catalyst is filtered off and evaporated.

Yield: 32.1 g quantitative
Yellow oil, rapidly becomes brown in air.

What is claimed is:

1. A 4-bromo-6-chloro-5-amino-2-pyridyl-ethanolamine of the formula

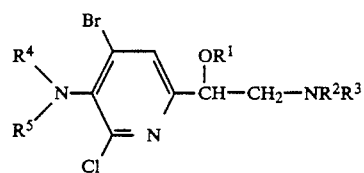

in which,
- $R^1$ stands for hydrogen or $C_{1-6}$-alkyl, or for carbonyl-$C_{1-6}$-alkyl, optionally substituted carbonylphenyl, sulphonyl-$C_{1-6}$-alkyl or optionally substituted sulphonylphenyl; or for tris-($C_1$-$C_{12}$-alkyl)-silyl or diphenyl-$C_{1-6}$-alkylsilyl,
- $R^2$ stands for hydrogen or $C_{1-6}$-alkyl,
- $R^3$ stands for hydrogen, optionally substituted branched $C_{3-6}$-alkyl, $C_{3-6}$-cycloalkyl or $C_{1-6}$-alkyl-phenyl, or
- $R^2$ and $R^3$, together with the nitrogen atom to which they are bonded, can stand for optionally substituted piperazinyl, morpholinyl, piperidinyl, and pyrrolidinyl,
- $R^4$ stands for hydrogen or $C_{1-6}$-alkyl and
- $R^5$ stands for hydrogen, $C_{1-6}$-alkyl, $C_{1-4}$-halogenoalkyl, $C_{1-6}$-alkylcarbonyl, optionally substituted benzoyl, $C_{1-6}$-alkylsulphonyl or optionally substituted phenylsulphonyl, wherein the possible substituents of the optionally substituted $R^1$, $R^3$, $R^2$ and $R^3$, together with the nitrogen atom to which they are bonded and $R^5$ radicals are:

cyano, halogen, hydroxyl, $C_{1-4}$-alkyl, $C_{1-4}$-halogenoalkyl, phenyl, $C_{1-4}$-alkoxy, $C_{1-4}$-halogenoalkoxy, $C_{1-4}$-alkylthio and $C_{1-4}$-halogenoalkylthio, and in the case where the substituents are on a phenyl radical, also methylenedioxy, ethylenedioxy, halogensubstituted methylenedioxy, and halogensubstituted ethylenedioxy, phenyl and phenoxy, or phenyl or phenoxy, which are substituted by cyano, halogen, hydroxyl, $C_{1-4}$-alkyl, $C_{1-4}$-halogenoalkyl, phenyl, $C_{1-4}$-alkoxy, $C_{1-4}$-halogenoalkoxy, $C_{1-4}$-alkylthio, $C_{1-4}$-halogenoalkylthio, methylenedioxy, ethylenedioxy, halogen-substituted methylenedioxy, halogen-substituted ethylenedioxy, and phenoxy.

2. A 4-bromo-6-chloro-5-amino-2-pyridyl-ethanolamine according to claim 1, in which:
- $R^1$ stands for hydrogen or $C_{1-6}$-alkyl,
- $R^2$ stands for hydrogen or $C_{1-4}$-alkyl,
- $R^3$ stands for hydrogen, $C_{3-6}$-alkyl which is unsubstituted or substituted by 1 to 5 halogen atoms, or $C_{1-6}$-alkyl-phenyl, which is unsubstited or substituted in the phenyl ring by halogen, $C_{1-4}$-alkyl, hydroxyl, $C_{1-4}$-alkoxy or unsubstituted or halogen-substituted methylenedioxy or ethylenedioxy,
- $R^4$ stands for hydrogen and
- $R^5$ stands for hydrogen.

3. A 4-bromo-6-chloro-5-amino-2-pyridylethanolamine according to claim 1, of the formula

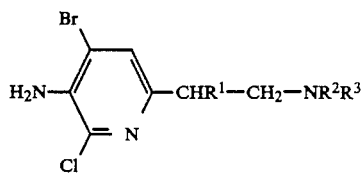

in which

| $R^1$ | $R^2$ | $R^3$ |
|---|---|---|
| OH | H | i-$C_3H_7$ |
| $OCH_3$ | H | i-$C_3H_7$ |
| OH | H | t-$C_4H_9$ |
| OH | H | t-$C_4H_8F$ |
| OH | H | —CH(CH₃)—CH₂—C₆H₄—COOH |
| OH | H | —CH(CH₃)—CH₂—C₆H₄—OCH₂—COOH |
| OH | H | —CH(CH₃)—CH₂—C₆H₄—OCH₂CH₂NH₂ |
| OH | H | —CH(CH₃)—(CH₂)₂—C₆H₄—OCH₂COOH |
| OH | H | —CH(CH₃)—(CH₂)₂—C₆H₄—COOH |
| OH | H | cyclohexyl-H |
| OH | H | —CH(CH₃)—CH₂—C₆H₄—O—CH₂—CH₂—OH |
| OH | H | —CH(CH₃)(CH₂—O—CH₃) |
| OH | H | —CH(CH₃)—CH₂—C₆H₅ |
| OH | H | —(CH₂)₃CH₃ |
| OH | H | —CH(Et)(Et) |
| OH | H | —CH₂—CH(CH₃)(CH₃) |
| OH | H | —C(CH₃)(Et)(CH₃) |

-continued
| R¹ | R² | R³ |
|---|---|---|
| OH | H | —CH₂—CH₂—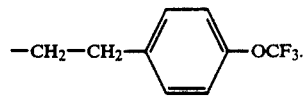—OCF₃. |
4. A 4-bromo-6-chloro-5-amino-2-pyridyl-ethanolamine according to claim 1 of the formula
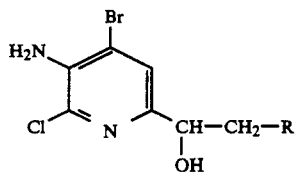
in which R is
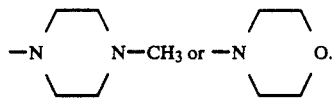
5. A yield-promoting composition for animals comprising a yield promoting effective amount of a 2-pyridyl-ethanolamine according to claim 1 and an acceptable carrier.
* * * * *